United States Patent [19]

Sciavolino

[11] 4,188,479

[45] Feb. 12, 1980

[54] SEMI-SYNTHETIC OLEANDOMYCIN DERIVATIVES-$C_8$ MODIFICATIONS

[75] Inventor: Frank C. Sciavolino, East Lyme, Conn.

[73] Assignee: Pfizer Inc., New York, N.Y.

[21] Appl. No.: 894,897

[22] Filed: Apr. 10, 1978

Related U.S. Application Data

[62] Division of Ser. No. 766,219, Feb. 7, 1977, Pat. No. 4,110,530, which is a division of Ser. No. 712,360, Aug. 6, 1976, Pat. No. 4,036,853.

[51] Int. Cl.$^2$ ............................................. C07H 17/08
[52] U.S. Cl. ................................. 536/9; 536/17 R; 424/180
[58] Field of Search ................................. 536/17, 9

[56] References Cited

U.S. PATENT DOCUMENTS

| | | | |
|---|---|---|---|
| 3,022,219 | 2/1962 | Celmer | 536/17 |
| 3,179,652 | 4/1965 | Celmer | 536/17 |

*Primary Examiner*—Johnnie R. Brown
*Assistant Examiner*—Blondel Hazel
*Attorney, Agent, or Firm*—Connolly and Hutz

[57] ABSTRACT

The novel $C_8$ modified oleandomycin compounds and the processes for their preparation are disclosed.

2 Claims, No Drawings

SEMI-SYNTHETIC OLEANDOMYCIN DERIVATIVES-C$_8$ MODIFICATIONS

CROSS-REFERENCE TO RELATED APPLICATION

This application is a division of application Ser. No. 766,219 filed Feb. 7, 1977 now U.S. Pat. No. 4,110,530 which in turn is a division of application Ser. No. 712,360 filed Aug. 6, 1976 and now U.S. Pat. No. 4,036,853.

BACKGROUND OF THE INVENTION

Oleandomycin, its production in fermentation broths and its use as an antibacterial agent were first described in U.S. Pat. No. 2,757,123, the disclosure of which is incorporated herein by reference. The naturally occurring compound is known to have the structure

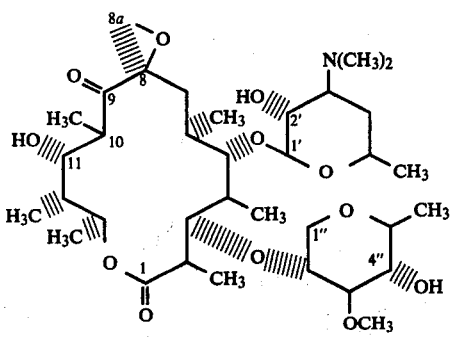

1.

The conventionally accepted numbering scheme and stereochemical representation for oleandomycin 1. and similar compounds is shown at a variety of positions.

Several synthetic modifications of this compound are known, particularly those in which from one to three of the free hydroxyl groups found at the 2′, 4″ and 11-positions are esterified as acetyl esters. In addition, there are described in U.S. Pat. No. 3,022,219 similar modifications in which the acetyl in the above-mentioned esters is replaced with another, preferably unbranched lower alkanoyl of two to six carbon atoms or trifluoroacetyl moiety.

Also known are semi-synthetic oleandomycins in which one or several of the hydrogens of the hydroxyl groups mentioned above are replaced with a tri(lower alkyl)silyl and preferably a trimethylsilyl group.

SUMMARY OF THE INVENTION

The novel compounds of the present invention consist of the products of sequential, synthetic transformations performed upon natural oleandomycin and its derivatives. In addition, the chemical methods used in these transformations have been discovered to operate on only the functional group being changed.

The compounds of the present invention are oleandomycin derivatives and have the structure

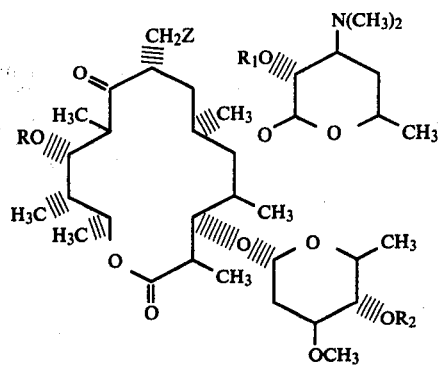

A and the pharmaceutically acceptable acid addition salts thereof wherein:

R is selected from the group consisting of hydrogen and n-alkanoyl having from two to three carbon atoms;

R$_1$ is selected from the group consisting of hydrogen and n-alkanoyl having from two to three carbon atoms;

R$_2$ is selected from the group consisting of hydrogen and n-alkanoyl having from two to three carbon atoms;

Z is selected from the group consisting of —N=CHN(R$_3$)$_2$, —N(R$_3$)$_2$, —NHR$_5$, —NH$_2$, —OR$_4$, —N$_3$, Cl and imidazol-1-yl;

R$_3$ is alkyl having from one to three carbon atoms;

R$_4$ is selected from the group consisting of hydrogen, alkanoyl having from two to six carbon atoms and SO$_2$R$_7$;

R$_5$ is selected from the group consisting of

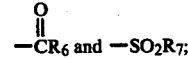

R$_6$ is selected from the group consisting of hydrogen, alkyl having from one to six carbon atoms, amino (—NH$_2$), alkylamino having from one to six carbon atoms, pyridyl, anilino, α-thienyl, and

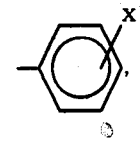

said substituent X being selected from the group consisting of hydrogen, halogen, alkyl having from one to four carbon atoms, alkoxycarbonyl having from one to four carbon atoms in the alkoxy group, CF$_3$, alkoxy having from one to four carbon atoms, CONH$_2$ and —NO$_2$; and R$_7$ is selected from the group consisting of alkyl having from one to six carbon atoms and

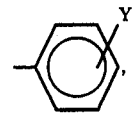

said substituent Y being selected from the group consisting of hydrogen, alkyl having from one to four carbon atoms, chloro and —CF$_3$.

The novel compounds of the present invention are able to combat infections caused by susceptible organisms and are valuable as antibiotic and antibacterial agents. Of interest in this connection are several preferred embodiments of the present invention. These embodiments include 8,8a-deoxy-8-hydroxymethyl oleandomycin and its esterified derivatives; that is, those derivatives in which from one to three of the hydroxyl groups at positions 2', 4" and 11 are esterified with alkanoyl groups having from two to three carbon atoms, 8,8a-deoxy-8-tosyloxymethyl oleandomycin and its esterified derivatives wherein the esterifying groups and their positions are defined as above, 8,8a-deoxy-8-aminomethyl oleandomycin and its esterified derivatives wherein the esterifying groups and their positions are defined as above, 8,8a-deoxy-8-N-acyl and N-sulfonyl aminomethyl oleandomycin and their esterified derivatives wherein the esterifying groups and their positions are defined as above, 8,8a-deoxy-8-N-(acetyl)aminomethyl oleandomycin and its esterified derivatives wherein the esterifying groups and their positions are defined as above, 8,8a-deoxy-8-N-(formyl)aminomethyl oleandomycin and its esterified derivatives wherein the esterifying groups and their positions are defined as above, 8,8a-deoxy-8-(dimethylaminomethylidenyl)aminomethyl oleandomycin and its esterified derivatives wherein the esterifying groups and their positions are defined as above, 8,8a-deoxy-8-chloromethyl oleandomycin and its esterified derivatives wherein the esterifying groups and their positions are defined as above, 8,8a-deoxy-8-(imidazol-1-yl)methyl oleandomycin and its esterified derivatives wherein the esterifying groups and their positions are defined as above and 8,8a-deoxy-8-azidomethyl oleandomycin and its esterified derivatives wherein the esterifying groups and their positions are defined as above.

DETAILED DESCRIPTION OF THE INVENTION

The novel oleandomycin compounds of the present invention are prepared from natural oleandomycin and its acylated derivatives in which from one to three of the hydroxyl groups at positions 2', 4" and 11 are acylated with alkanoyl groups having from two to three carbon atoms. The methods by which the acylated derivatives of natural oleandomycin are prepared are described in U.S. Pat. No. 3,022,219.

Structure A above illustrates the configuration of these oleandomycin compounds. It can be seen from a comparison of structure A and oleandomycin that the differences between the compounds of the present invention and oleandomycin are contained in partial structure B and the groups R, $R_1$ and $R_2$.

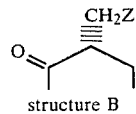

structure B

Therefore, the compounds of the present invention will be represented herein by the partial structure B.

For the purposes of the following discussion, esterified derivatives shall be taken to mean oleandomycin compounds in which from one to three of the hydroxyl groups at positions 2', 4" and 11 are esterified with n-alkanoyl groups having from two to three carbon atoms. In addition, any of the unesterified (at positions 2', 4" and 11) compounds of the present invention are convertible, unless otherwise stated, into any of their claimed, esterified derivative as defined above according to the method of U.S. Pat. No. 3,022,219 and this process is hereby disclosed.

It is also hereby disclosed that the claimed esterified derivatives of the oleandomycin compound-starting materials for the processes of the present invention are also functionable in those processes unless otherwise stated.

The process shown in reaction 1 for preparation of the new 8,8a-deoxy-8-hydroxymethyl oleandomycin, formula C, or its 2'-acyl or 2',4"-diacyl derivatives is the reductive cleavage of the 8,8a-epoxide of natural oleandomycin, 2'-acyloleandomycin or 2',4"-diacyloleandomycin with any reagent which performs a selective reduction on the epoxide to yield the primary alcohol. Typical reagents include the metal amalgams such as zinc amalgam, magnesium amalgam and especially aluminum amalgam.

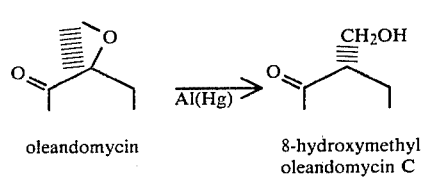

oleandomycin     8-hydroxymethyl oleandomycin C

1.

The typical procedure for the process of reaction 1 comprises allowing contact between oleandomycin or its acylated derivatives above and the metal amalgam in an oleandomycin-soluble solvent such as alkanol, ether, moist ether, benzene, aqueous alkanol, tetrahydrofuran, aqueous tetrahydrofuran, dioxane, aqueous dioxane or mixtures thereof until the reaction is essentially complete. The temperature range for the reaction includes ambient temperature to that of refluxing solvent and the typical procedure will call for ambient temperature.

After separation of the complex inorganic salts, the product can be isolated and purified according to appropriate methods which will depend upon the product's physical characteristics. The techniques that can be employed include recrystallization, lyophilization, chromatography, high pressure liquid chromatography and extraction.

If desired, the 8-hydroxymethyl group of the oleandomycin, formula C, 2',4"-diacyl derivative can be protected with a silyl group such as trimethyl silyl or preferably dimethyl-t-butyl silyl according to the methods reported for attachment of such groups. Then, any of the protected compounds can, if desired, be converted into the triesterified derivatives, as defined above, by the method of U.S. Pat. No. 3,022,219, followed by removal of the 8-hydroxymethyl protecting group according to common and known procedures.

The preparation of the new 8,8a-deoxy-8-chloromethyl oleandomycin, formula D, or its esterified derivatives is accomplished by the process, shown in reaction 2, of contacting 8,8a-deoxy-8-hydroxymethyl oleandomycin or its esterified derivatives with N-chlorosuccinimide and triphenyl phosphine in a polar, aprotic solvent such as dimethylformamide at temperatures from −30° C. to ambient.

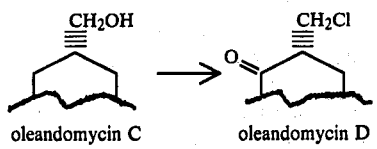

oleandomycin C → oleandomycin D        2.

After the reaction is essentially complete, the product can be isolated by partition of the reaction residue between a buffered, basic aqueous phase and an organic phase in which the product is soluble. Final purification can be achieved by chromatographic, crystallization, lyophilization or high pressure liquid chromatographic techniques, the choices of which will depend upon the product's physical characteristics.

The preparation, reaction 3, of the new 8,8a-deoxy-8-(sulfonyloxy)methyl oleandomycin, formula E, or its esterified derivatives is accomplished by contacting 8,8a-deoxy-8-hydroxymethyl oleandomycin, formula C, or its esterified derivatives with a sulfonating agent which can be any sulfonyl chloride. The preferred sulfonyl chlorides are those compounds of the formula $R_7SO_2Cl$ wherein $R_7$ is defined as above.

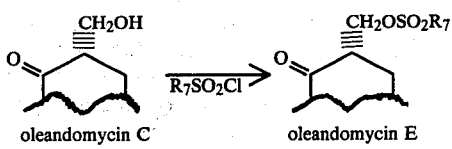

oleandomycin C → oleandomycin E        3.

The typical procedure which functions to allow reaction 3 to proceed is as follows. If a sulfonyl chloride is employed as the sulfonating agent, formation of oleandomycin, formula E, will typically be accomplished by contacting oleandomycin, formula C, or its esterified derivatives with about one equivalent of sulfonyl chloride in an organic amine solvent such as triethylamine, pyridine or lutidine, diluted, if desired, with an inert organic solvent such as chloroform, benzene, methylene chloride or toluene.

The product can then be isolated by partitioning the reaction mixture between a buffered, basic aqueous phase and an organic phase in which the product is soluble, followed by purification of the product by chromatographic, crystallization or lyophilization techniques, the choice of which will depend upon the product's physical characteristics.

The preparation of the new 8,8a-deoxy-8-(acyloxy)methyl oleandomycin, formula F, or its esterified derivatives is accomplished in a manner similar to the sulfonyl chloride procedure above by contacting 8,8a-deoxy-8-hydroxymethyl oleandomycin, formula C, or its esterified derivatives with an acylating agent of the formula $$(C_vH_{2v+1}\underset{\underset{O}{\|}}{C})_2O \text{ or } C_vH_{2v+1}\underset{\underset{O}{\|}}{C}Cl,$$

said v being an integer from one to five.

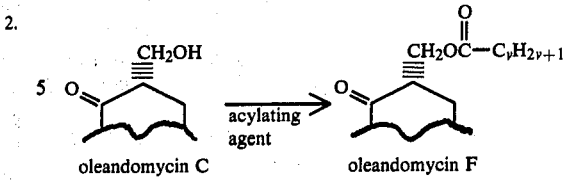

oleandomycin C → oleandomycin F        4.

Additionally, if an anhydride or mixed anhydride is employed as the acylating agent, contact of oleandomycin, formula C, or its esterified derivatives with about one equivalent of that type of acylating agent in any inert organic solvent in which the oleandomycin, formula C, and acylating agent are soluble will cause the formation of oleandomycin, formula F.

The new 8,8a-deoxy-8-(imidazol-1-yl)methyl oleandomycin, formula G, or its esterified derivatives is prepared by displacement of the 8-sulfonyloxy group, preferably 8-tosyloxy, of 8,8a-deoxy-8-(sulfonyloxy)methyl oleandomycin, formula F, or its esterified derivatives with imidazole.

A typical procedure calls for warming a solution of oleandomycin, formula F, and imidazole in a polar, aprotic solvent such as dimethylformamide or dimethyl sulfoxide at temperatures from 25° C. to 100° C. until the displacement is essentially complete. Isolation of the product can be achieved by partition of the reaction residue between a buffered, basic aqueous phase and an organic phase in which the product is soluble, typically ethyl acetate. The resulting crude product can then be purified by the techniques of chromatography, recrystallization or lyophilization, the choice of which will depend upon the product's physical characteristics.

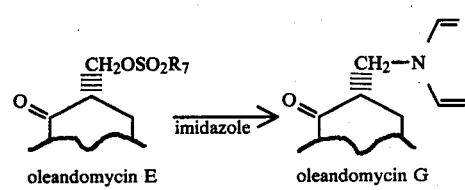

oleandomycin E → oleandomycin G        5.

In a similar fashion, the sulfonyloxy group, preferably tosyloxy, of oleandomycin F or its esterified derivatives can be displaced with azide ion thus allowing the preparation of new 8,8a-deoxy-8-azidomethyl oleandomycin H or its esterified derivatives.

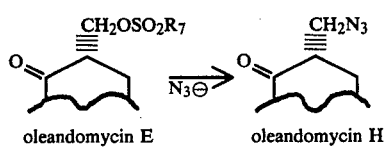

oleandomycin E → oleandomycin H        6.

The compounds of the present invention wherein Z is an amine or amine derivative are prepared from 8,8a-deoxy-8-azidomethyl oleandomycin or its esterified derivatives by reduction of the azide under various conditions and, if desired in certain cases, condensation of the resulting 8,8a-deoxy-8-aminomethyl oleandomycin or its esterified derivatives with amidation, sulfonamidation or imination agents. These oleandomycin compounds resulting from such transformations consist of 8,8a-deoxy-8-aminomethyl oleandomycin I, 8,8a-deoxy-8-N-(dialkyl)aminomethyl oleandomycin, formula J, 8,8a-deoxy-8-N-(dialkylaminomethylidenyl- )aminomethyl oleandomycin, formula K, 8,8a-deoxy-8-N-(R_6CO)-aminomethyl oleandomycin, formula L, 8,8a-deoxy-8-N-(R_7SO_2)aminomethyl oleandomycin, formula M, and their esterified derivatives. The preparation of each of these oleandomycin compounds is described below.

Under normal, low pressure (up to 100 p.s.i.) catalytic hydrogenation conditions, 8-azidomethyl oleandomycin, formula H, or its esterified derivatives is reduced to 8,8a-deoxy-8-aminomethyl oleandomycin, formula I, or its esterified derivatives according to reaction 7.

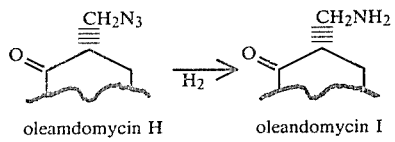

A typical method employs oleandomycin, formula H, soluble solvents such as water, methanol, ethanol, isopropanol, or mixtures thereof and noble metal catalysts such as palladium on carbon, platinum oxide and the like for the hydrogenation of oleandomycin, formula H, to oleandomycin, formula I. After the hydrogenation is essentially complete, the product may be isolated by chromatography, lyophilization, or recrystallization of the reaction residue, the selection of which will depend upon the product's physical characteristics.

The N-dialkyl 8,8a-deoxy-8-aminomethyl oleandomycin, formula J, compounds or their esterified derivatives are formed from 8,8a-deoxy-8-azidomethyl oleandomycin, formula H, or its esterified derivatives by catalytic reductive alkylation as shown in reaction 8.

Using the same catalytic hydrogenation method as that described above for the formation of oleandomycin, formula I, and including in the solvent an appropriate amount of n-alkanal having from one to three carbon atoms, hydrogenation of 8-azidomethyl oleandomycin, formula H, or its esterified derivatives forms in situ 8,8a-deoxy-8-aminomethyl oleandomycin, formula I, or its esterified derivatives, which then is reductively alkylated with the n-alkanal.

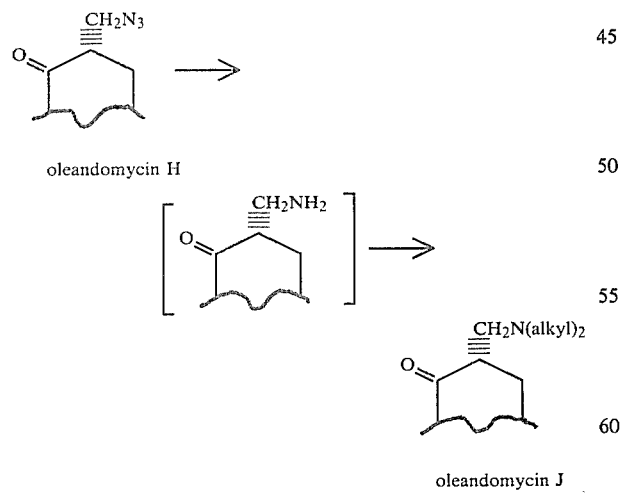

After the alkylated derivative has been formed by this process, the product can be isolated by partition of the reaction residue between a buffered, basic aqueous phase and an organic phase in which the product is soluble. It is then purified by recrystallization or chromatographic techniques, the choice of which will depend upon the product's physical characteristics.

The imine derivatives, formula K, of 8,8a-deoxy-8-aminomethyl oleandomycin, formula I, or its esterified derivatives are formed from the 8-aminomethyl compound, formula I, or its esterified derivatives by contacting it with dialkylformamide dimethylacetal having from one to three carbon atoms in the alkyl group in a polar, aprotic solvent such as dimethylformamide, dimethyl sulfoxide or dialkylformamide as shown in reaction 9.

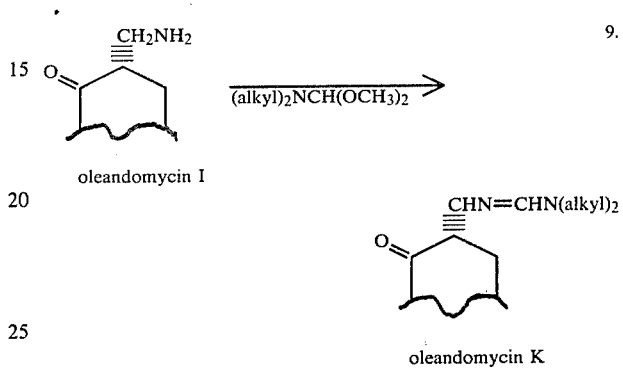

After the reaction is essentially complete, it is quenched by pouring it onto ice water. After extraction, or use of other appropriate isolation techniques, the product can be purified by chromatography or recrystallization, the choice of which will depend upon the product's physical characteristics.

The amide

(R_6C—)

and sulfonamide (R_7SO_2—) derivatives, formulae L and M, respectively, of 8,8a-deoxy-8-aminomethyl oleandomycin, formula I, or its esterified derivatives are formed by contact of oleandomycin, formula I, or its esterified derivatives with an amidating or sulfonamidating agent of the formula:

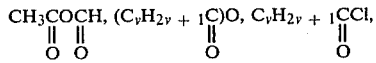

HNCO, alkyl-NCO having from one to four carbon atoms in the alkyl group, PhNCO, nicotinyl chloride, isonicotinyl chloride, picolinyl chloride, α-thienyl chloride, alkyl-SO_2Cl having from one to five carbon atoms in the alkyl group,

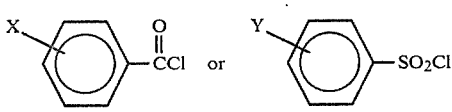

wherein: v is an integer from one to five; X is selected from the group consisting of hydrogen, halogen, alkyl having from one to four carbon atoms, alkoxycarbonyl having from one to four carbon atoms in the alkoxy group, $CF_3$, alkyloxy having from one to four carbon atoms, —$CONH_2$ and —$NO_2$; and Y is selected from the group consisting of hydrogen, chloro, alkyl having from one to four carbon atoms and —$CF_3$.

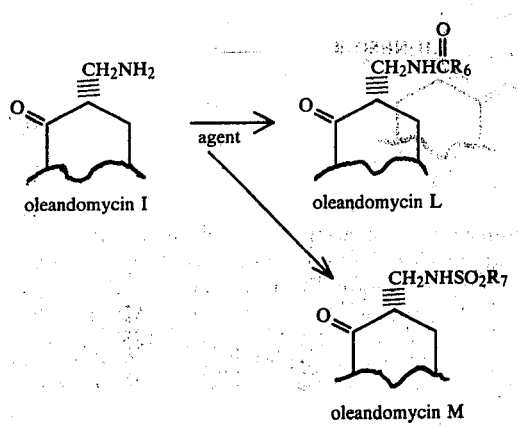

The usual procedure employs dilute alkali or an organic amine such as pyridine, triethylamine or lutidine as a base in the case of the acid and sulfonyl chloride agents in order to neutralize the formed hydrogen chloride. Selection of the base will depend upon the type of product and the agent used. In addition, the organic amine can also function as solvent or it can be diluted with an inert organic solvent such as chloroform, benzene or methylene chloride. Water miscible or water immiscible solvents such as tetrahydrofuran or chloroform are both employed with the dilute alkali base. In the case of urea formation ($R_6$=$NH_2$, NH-alkyl or PhNH), the solvent chosen must be one which will not react with the isocyanate starting material. In the case of the anhydride and mixed anhydride agents, a solvent in which both the oleandomycin, formula I, and the agent are soluble can be employed with success, and a base is not necessary. Such solvents include methanol, ethanol, ethyl acetate, acetone, isopropanol, n-propanol, chloroform, methylene chloride, tetrahydrofuran, dioxane, dimethoxyethane and methyl ethyl ketone. The temperature range for the reaction in all cases includes that of an ice bath to that of the refluxing solvent and typically will be ambient temperature. After the reaction is essentially complete, the reaction residue can be partitioned between a buffered, basic aqueous phase and an organic phase in which the product is soluble, typically chloroform or ethyl acetate. The resulting crude, isolated product can then be purified by chromatography, lyophilization, recrystallization, high pressure liquid chromatography or extraction/evaporation techniques, the choice of which will depend upon the product's physical characteristics.

The processes described above together produce all the novel products of the present invention. From the description of these processes, it is evident that they are inter-related and dependent, in some cases, upon a previously formed product of the present invention. That inter-relation is presented in Scheme A wherein the integers indicate the particular reaction of the processes above.

Scheme A natural oleandomycin

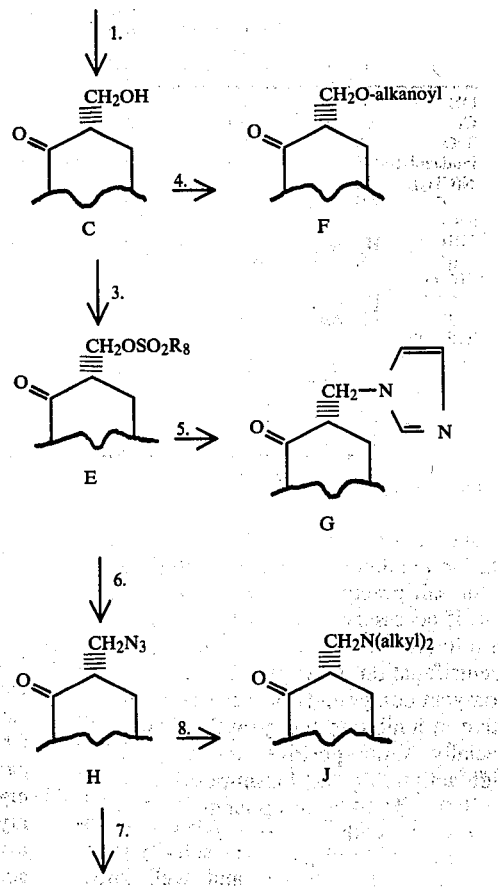

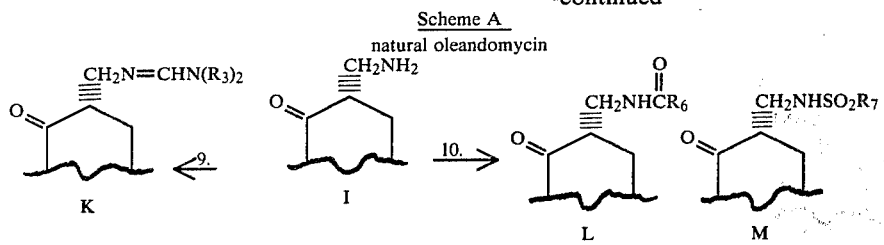

Scheme A

The pharmaceutically-acceptable acid addition salts of the oleandomycin compounds of the present invention are prepared by contacting a solution of a compound of the present invention in a suitable solvent such as acetone with a stoichiometric equivalent of a mineral acid such as hydrochloric, hydrobromic, phosphoric or sulfuric acid; an organic acid selected from the group consisting of aspartic, citric, tartaric, gluconic, succinic and stearic acid; or an alkyl sulfuric acid such as lauryl sulfuric acid. The salt precipitates after the neutralization reaction or, if necessary, after partial evaporation of the reaction solution. The product may be recovered by filtration, centrifugation or lyophilization.

The oleandomycin compounds of the present invention are effective in inhibiting the growth of microorganisms, especially Gram-positive microorganisms. That is, the high activity against Gram-positive organisms in general shown by these compounds can be contrasted in some respects with the lower activity shown against certain especially virulent and well known Gram-negative organisms. The following table illustrates the in vitro antibiotic spectrum of the compound of the instant invention. The tests were run according to the "minimum inhibitory concentration" (MIC) method of Ericsson and Sherris [H. M. Ericsson and J. C. Sherris, Acta. Pathol. Microbiol. Scand. Suppl., 217B, 64 (1971)].

TABLE I

MIC Values (meg./ml.) of some semi-synthetic oleandomycin derivatives - $C_8$ modifications

AR = H

| Z | $R_1$ | $R_2$ | Staph.aureus 01A005* | Staph.aureus 01A400R* | St-rep.py. 020263A226+ | E.coli 53A009+ | Klebsiella pn. 58D009+ | Salm.typhm. 66C001+ | Neisseriae Sicca |
|---|---|---|---|---|---|---|---|---|---|
| OH | Ac | H | 6.25 | 12.5 | 1.56 | >200 | >200 | >200 | 0.39 |
| Cl | H | Ac | 3.12 | 50 | 1.56 | 200 | >200 | >200 | ≤0.1 |
| TsO | Ac | H | 100 | >200 | 3.12 | >200 | >200 | >200 | 3.12 |
| imidazol-1-yl | H | Ac | 0.39 | 6.25 | — | >200 | >200 | >200 | ≤0.1 |
| N(CH$_3$)$_2$ | H | Ac | 25 | 50 | 50 | >200 | >200 | >200 | 1.56 |
| O‖NHCH | H | Ac | 6.25 | 50 | 1.56 | >200 | >200 | >200 | 0.20 |
| O‖NHCPh | H | Ac | >200 | >200 | >200 | >200 | >200 | >200 | 6.25 |
| O‖NHC-3-Py | H | Ac | 25 | 100 | 12.5 | >200 | >200 | >200 | 1.56 |
| O‖NHCNH$_2$ | H | Ac | 50 | >200 | 50 | >200 | >200 | >200 | >200 |
| NH$_2$ | H | Ac | 6.25 | 25 | 50 | >200 | >200 | >200 | ≤0.10 |
| N$_3$ | H | Ac | 3.1 | 12.5 | 3.1 | >200 | >200 | >200 | 0.20 |

*= Gram-positive
+= Gram-negative

The ability of some compounds of the present invention to protect against in vivo infections was determined by subcutaneous or oral administration to mice infected with Staph. aureus 01A005. Using the test procedure of Retsema [J. A. Retsema, et al., Antimicr. Agents and Chemother., 9, 975 (1976)] it was determined that, in particular, 8,8a-deoxy-8-azidomethyl-4″-acetyloleandomycin, 8,8a-deoxy-8-hydroxymethyl-2′-acetyloleandomycin, 8,8a-deoxy-8-chloromethyl-4″-acetyloleandomycin, 8,8a-deoxy-8-(imidazol-1-yl)methyl-4″-acetyloleandomycin and 8,8a-deoxy-8-(N-acetyl- )aminomethyl-4''-acetyloleandomycin all gave protection against infection which was comparable to natural oleandomycin.

For effective prophylactic and anti-infectious in vivo use, the oleandomycin compounds of the present invention may be administered either alone or in combination with a pharmaceutically-acceptable carrier, by the oral or parenteral routes. The ultimate choice of route and dose is made by the attending physician and is based upon the patient's unique condition. However, the usual dosage for administration to humans lies in the range of approximately 500–2000 mg. P.O. per day, and preferably in about one to four doses. However, this dosage may vary somewhat with the weight of the subject being treated; in general, about 10–40 mg./kg. of body weight per day can be employed.

The compounds of this invention can be combined with inert pharmaceutical excipients such as lactose, mannitol and starch, and formulated into dosage forms such as tablets, capsules and the like. For parenteral administration, these compounds can be formulated with an inert, parenterally acceptable vehicle such as water, saline, sesame oil, propylene glycol and the like. These various pharmaceutical dosage forms are compounded by methods well known to the pharmacist's art.

EXAMPLE 1

8,8a-Deoxy-8-hydroxymethyl-2',4''-diacetyloleandomycin 1

To a suspension of 10 g. of amalgamated aluminum (prepared from one-quarter inch squares of aluminum foil by the method of Ferris, Sanchez and Manusco, *Org. Syn. Coll. Vol. V*, page 32) in 200 ml. of 10% aqueous tetrahydrofuran at room temperature and contained in a 1 liter, three-necked, round bottom flask equipped with a mechanical stirrer was added dropwise a solution of 5.0 g. (6.4 mmoles) of 2',4''-diacetyloleandomycin in 50 ml. of 10% aqueous tetrahydrofuran. The resulting suspension was stirred at room temperature for 48 hrs. and the aluminum salts separated by filtration through diatomaceous earth. The filtrate was added to a mixture of ethyl acetate and water and the organic phase was separated and washed twice with water, once with saturated sodium chloride solution, dried over anhydrous sodium sulfate, filtered and the solvent evaporated from the filtrate under reduced pressure. The resulting material was placed on a column of silica gel and eluted with ethyl acetate to yield 850 mg. of the title compound as a white foam. The NMR of the product exhibited the following characteristic resonances:

NMR—(CDCl$_3$) δppm: 5.43 (1H) m; 3.40 (3H) s; 2.25 (6H) s; 2.10 (3H) s; 2.06 (3H) s.

By employing the procedure of Example 1, the following 8,8a-deoxy-8-hydroxymethyl-2'-acyloleandomycins or 8,8a-deoxy-8-hydroxymethyl-2',4''-diacyloleandomycins can be made by substituting for 2',4''-diacetyloleandomycin the appropriate oleandomycin in which from one to two of the free hydroxyl groups at positions 2' and 4'' are esterified with alkanoyl groups having from two to three carbon atoms: 8,8a-deoxy-8-hydroxymethyl-2'-propionyloleandomycin and 8,8a-deoxy-8-hydroxymethyl-2',4''-di-n-propionyloleandomycin.

In addition, formation of 8,8a-deoxy-8-hydroxymethyl-2',4'',11-triacyl oleandomycin derivatives can be accomplished by first preparing the 8-(dimethyl-t-butyl silyloxy)methyl derivative of compound 1 or its 2',4''-dipropionyl analog according to the procedure of Corey, *J. Am. Chem. Soc.*, 94, 6190 (1974) and then acylating it according to the procedures of U.S. Pat. No. 3,022,219 followed by cleavage of the silyl group with tetra-n-butyl ammonium fluoride.

EXAMPLE 2

8,8a-Deoxy-8-hydroxymethyl-2'-acetyloleandomycin 2

By employing the procedure of Example 1, 2'-acetyloleandomycin was converted into the title compound. It exhibited the following characteristic NMR spectrum:

NMR CDCl$_3$ δppm: 5.46 (1H) m; 3.46 (3H) s; 2.30 (6H) s; 2.08 (3H) s.

EXAMPLE 3

8,8a-Deoxy-8-hydroxymethyloleandomycin 3

By employing the procedure of Example 1, oleandomycin was converted into the title compound. It had the following characteristic resonances in the NMR spectrum:

NMR CDCl$_3$ δppm: 5.40 (1H) m; 4.95 (1H) m; 4.20 (1H) d; 3.36 (3H) s; 2.23 (6H) s.

EXAMPLE 4

8,8a-Deoxy-8-tosyloxymethyl-2',4''-diacetyloleandomycin 4

To a solution of p-toluenesulfonyl chloride (988 mg.; 5.16 mmoles) in 3 ml. of pyridine cooled to 0° C. was added 2.0 g. (2.58 mmoles) of 8,8a-deoxy-8-hydroxymethyl-2',4''-diacetyloleandomycin 1 as a solid in one portion. After stirring at 0° C. for three hours, the solution was poured into a mixture of ethyl acetate and water and the pH adjusted to 8.5 with saturated sodium bicarbonate solution. The organic phase was separated and washed successively with water, dilute hydrochloric acid of pH 3.5, water, sodium bicarbonate solution of pH 8.5, and saturated sodium chloride solution. Evaporation under reduced pressure of the organic layer gave 2.30 g. of white foam which was chromatographed on a 15 by 8.5 cm. column of silica gel. Elution with ethyl acetate and acetone in a 9:1 ratio gave 1.62 g. of the title compound as a white foam. The NMR exhibited the following characteristic resonances:

NMR—(CDCl$_3$) δppm: 7.56 (4H) q; 5.35 (1H) m; 3.35 (3H) s; 2.43 (3H) s; 2.25 (6H) s; 2.10 (3H) s; 2.05 (3H) s.

EXAMPLE 5

8,8a-Deoxy-8-tosyloxymethyl-2'-acetyloleandomycin 5

Following the procedure of Example 4, the title compound was prepared from 8,8a-deoxy-8-hydroxymethyl-2'-acetyloleandomycin 2. The NMR exhibited the following characteristic resonances:

NMR CDCl$_3$ δppm: 7.56 (4H); 5.38 (1H) m; 3.43 (3H) s; 2.46 (3H) s; 2.30 (6H) s; 2.05 (3H) s.

By employing the procedure of Example 4, the following 8-tosyloxymethyloleandomycins can be prepared by substituting for oleandomycin 1 the appropriately esterified 8,8a-deoxy-8-hydroxymethyl-oleandomycin; that is, an 8-hydroxymethyloleandomycin compound in which from one to three of the free hydroxyl groups at positions 2', 4'' and 11 are esterified with alkanoyl groups having from two to three carbon atoms, and by substituting the appropriate sulfonyl chloride for p-toluenesulfonyl chloride: 8,8a-deoxy-8-methylsulfonoxymethyl-2'-propionyloleandomycin, 8,8a-deoxy-8-propylsulfonoxymethyl-2',4''-diacetyloleandomycin, 8,8a-8-deoxy-m-trifluoromethylphenylsulfonoxymethyl-2',4''-diacetyloleandomycin, 8,8a-deoxy-8-tosyloxymethyl-2',4'',11-triacetyloleandomycin, 8,8a-deoxy-8-tosyloxymethyl-2',4''-11-tripropionyloleandomycin and 8,8a-deoxy-8-(p-chlorophenylsulfonoxy)methyl-2',4''-diacetyloleandomycin.

The procedure of Example 4 can also be used to acylate 8,8a-deoxy-8-hydroxymethyl-2',4''-diacyloleandomycin and its other appropriately esterified derivatives at the 8-hydroxymethyl position by substituting the appropriate acid chloride for tosyl chloride. In this case, the products obtained will be the alkanoyl esters at the 8a-position instead of tosyloxy derivatives at the 8a-position as they are in Example 4, e.g., compounds such as

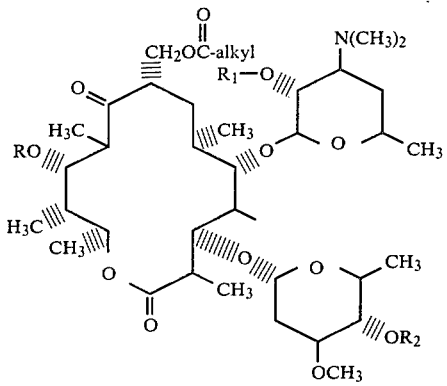

| R | $R_1$ | $R_2$ | alkyl |
|---|---|---|---|
| hydrogen | acetyl | acetyl | methyl |
| acetyl | acetyl | acetyl | propyl |
| propionyl | propionyl | propionyl | butyl |

These products can also be prepared by substituting the appropriate anhydride in place of the acid chloride. In this case, it will be convenient but not necessary to employ pyridine as a solvent. Other common inert organic solvents such as chloroform and methylene chloride can also be employed here.

EXAMPLE 6

8,8a-Deoxy-8-hydroxymethyl-4''-acetyloleandomycin 6

A solution of 3.43 g. (4.4 mmoles) of 8,8a-deoxy-8-hydroxymethyl-2',4''-diacetyloleandomycin 1 in 50 ml. of methanol was stirred at ambient temperature for 20 hours. Evaporation of the solvent under reduced pressure gave the title compound as a white foam. The NMR exhibited the following characteristic resonances:

NMR—(CDCl$_3$) δppm: 5.43 (1H) m; 3.35 (3H) s; 2.28 (6H) s; 2.08 (3H) s.

The following oleandomycins can also be prepared according to the procedure of Example 6 by substitution of the appropriate oleandomycin for oleandomycin 1: 8,8a-deoxy-8-hydroxymethyl-4''-propionyloleandomycin and 8,8a-deoxy-8-hydroxymethyl-4'',11-diacetyloleandomycin.

EXAMPLE 7

8,8a-Deoxy-8-tosyloxymethyloleandomycin 7

By employing the procedure of Example 6, 8,8a-deoxy-8-toxyloxymethyl-2'-acetyloleandomycin was converted into the title compound. It exhibited the following characteristic NMR resonances:

NMR (CDCl$_3$) δppm: 7.56 (4H) q; 5.43 (1H) m; 3.40 (3H) s; 2.43 (3H) s; 2.31 (6H) s.

EXAMPLE 8

8,8a-Deoxy-8-tosyloxymethyl-4''-acetyloleandomycin 8

By employing the procedure of Example 6, 8,8a-deoxy-8-tosyloxymethyl-2',4''-diacetyloleandomycin was converted into the title compound. It exhibited the following characteristic NMR spectrum resonances:

NMR (CDCl$_3$) δppm: 7.56 (4H) q; 5.38 (1H) m; 3.36 (3H) s; 2.43 (3H) s; 2.31 (6H) s; 2.10 (3H) s.

Also by employing the procedure of Example 6, the following oleandomycins can be prepared by substituting the appropriately esterified 8,8a-deoxy-8a-tosyloxymethyloleandomycin for oleandomycin 8: 8,8a-deoxy-8-tosyloxymethyl-4'',11-diacetyloleandomycin, 8,8a-deoxy-8-tosyloxymethyl-4''-propionyloleandomycin and 8,8a-deoxy-8-tosyloxymethyl-4'',11-dipropionyloleandomycin.

EXAMPLE 9

8,8a-Deoxy-8-azidomethyl-4''-acetyloleandomycin 9

A solution of 2.65 g. (3 mmoles) of 8,8a-deoxy-8-tosyloxymethyl-4''-acetyloleandomycin 8 in 30 ml. of dimethylsulfoxide contained in a 200 ml. three-necked round bottom flask equipped with a magnetic stirrer, thermometer and a nitrogen inlet was treated with 585 mg. (9 mmoles) of solid sodium azide in one portion. The flask was immersed in an oil bath and heated at 50° C. for 5.5 hours, then the contents were poured into a mixture of ice, water and ethyl acetate and the pH adjusted to 8.5 with sodium bicarbonate. The organic phase was separated and washed twice with equal volumes of water, once with an equal volume of saturated sodium chloride solution, dried over anhydrous sodium sulfate, filtered and the solvent evaporated from the filtrate under reduced pressure to give 2.25 g. of the title compound as a white foam. It produced a strong band in the infrared at 2095 cm$^{-1}$ and exhibited the following characteristic resonances in the NMR:

NMR (CDCl$_3$) δppm: 5.46 (1H) m; 3.33 (3H) s; 2.28 (6H) s; 2.10 (3H) s.

By employing the procedure of Example 9, the following oleandomycins can be prepared by substitution of the appropriately esterified 8,8a-deoxy-8-tosyloxymethyloleandomycin for oleandomycin 8: 8,8a-deoxy-8-azidomethyl-2',4''-dipropionyloleandomycin, 8,8a-deoxy-8-azidomethyl-4''-propionyloleandomycin, 8,8a-deoxy-8-azidomethyl-4'',11-diacetyloleandomycin, 8,8a-deoxy-8-azidomethyl-11-acetyloleandomycin, 8,8a-deoxy-8-azidomethyl-4'',11-dipropionyloleandomycin and 8,8a-deoxy-8-azidomethyl-2',4'',11-triacetyloleandomycin.

EXAMPLE 10

8,8a-Deoxy-8-azidomethyloleandomycin 10

By employing the procedure of Example 9, 8,8a-deoxy-8-tosyloxymethyloleandomycin 7 was converted into the title compound. Its infrared spectrum showed a strong band at 2100 cm$^{-1}$ and its NMR spectrum had the following characteristic resonances:

NMR (CDCl$_3$) δppm: 5.11 (1H) m; 3.45 (3H) s; 2.30 (6H) s.

EXAMPLE 11

8,8a-Deoxy-8-aminomethyl-4″-acetyloleandomycin 11

To a solution of 9.34 g. (12.3 mmoles) of 8,8a-deoxy-8-azidomethyl-4″-acetyloleandomycin 9 in 200 ml. of methanol was added 9.0 g. of 10% palladium on charcoal and the mixture was hydrogenated on a shaker hydrogenation apparatus for 1 hour. After removal of the catalyst from the reaction solution by filtration through diatomaceous earth and evaporation of the solvent from the filtrate under reduced pressure, the residue was chromatographed on a 80×4.5 cm. column of Sephadex LH-20 (Pharmacia Fine Chemicals, Piscataway, N.J.) by elution with tetrahydrofuran which produced 7.6 g. of the title compound as a white foam. It exhibited the following characteristic resonances in the NMR:

NMR (CDCl$_3$) $\delta$ppm: 5.30 (1H) m; 3.36 (3H) s; 2.30 (6H) s; 2.10 (3H) s.

EXAMPLE 12

8,8a-Deoxy-8-aminomethyloleandomycin 12

By employing the procedure of Example 11, 8,8a-deoxy-8-azidomethyl oleandomycin 10 was converted into the title compound. It exhibited the following characteristic NMR partial spectrum:

NMR (CDCl$_3$) $\delta$ppm: 5.13 (1H) m; 3.38 (3H) s; 2.26 (6H) s.

Similarly, the following compounds can be prepared: 8,8a-deoxy-8-aminomethyl-4′-propionyloleandomycin, 8,8a-deoxy-8-aminomethyl-4″,11-diacetyloleandomycin, 8,8a-deoxy-8-aminomethyl-11-acetyloleandomycin, 8,8a-deoxy-8-aminomethyl-4″-propionyloleandomycin, 8,8a-deoxy-8-aminomethyl-4″,11-dipropionyloleandomycin and 8,8a-deoxy-8-aminomethyl-11-acetyloleandomycin.

EXAMPLE 13

8,8a-Deoxy-8-chloromethyl-4′-acetyloleandomycin 13

A solution of 2.5 g. (3.23 mmoles) of 8,8a-deoxy-8-hydroxymethyl-2′,4″-diacetyloleandomycin 1 in 8 ml. of dimethylformamide contained in a 50 ml. 3-necked round bottom flask equipped with a magnetic stirrer, thermometer and nitrogen inlet, was cooled to 0° C. and treated with 861 mg. (6.46 mmoles) of N-chlorosuccimide. After stirring at 0° C. for ten minutes, the solution was cooled to −10° C. and 1.69 g. (6.46 mmoles) triphenylphosphine was added as a solid in small portions over a 30 minute period while maintaining the temperature of the solution between −10° and 0° C. When the addition was complete, the reaction mixture was allowed to warm to room temperature and stirring was continued for 30 minutes. The mixture was then poured into a two phase mixture of ethyl acetate and water, the pH adjusted to 8.5 and the organic phase was washed with water and saturated sodium chloride solution. The organic phase was dried over anhydrous sodium sulfate, filtered to remove the drying agent and the solvent evaporated from the filtrate under reduced pressure to yield 2.6 g. of a white solid. This material was taken up in 50 ml. of methanol and stirred at room temperature for 20 hours. The solvent was evaporated from this reaction solution under reduced pressure and the residue was chromatographed on Sephadex LH-20 (Pharmacia Fine Chemicals, Piscataway, N.J.) with methanol eluent to give 1.24 g. of the title compound as a white foam. It showed the following characteristic resonances in the NMR:

NMR (CDCl$_3$) $\delta$ppm: 5.43 (1H) m; 3.33 (3H) s; 2.28 (6H) s; 2.06 (3H) s.

EXAMPLE 14

8,8a-Deoxy-8-dimethylaminomethyl-4″-acetyloleandomycin 14

To a solution of 1.51 g. (2.0 mmoles) of 8,8a-deoxy-8-azidomethyl-4″-acetyloleandomycin 9 in 30 ml. of methanol was added 1.5 ml. of a 37% aqueous solution of formaldehyde (~20 mmoles of formaldehyde) and 1.5 g. of 10% palladium on carbon and the mixture was hydrogenated on a shaker hydrogenation apparatus at 50 psi overnight. After removal of the catalyst from the reaction slurry by filtration through diatomaceous earth and evaporation of the solvent from the filtrate under reduced pressure, the residue was crystallized from ethyl acetate and then recrystallized from isopropyl alcohol to give 800 mg. of the title compound, m.p. 180.5°–182° C. It showed the following characteristic resonances in the NMR:

NMR (CDCl$_3$) $\delta$ppm: 5.53 (1H) m; 3.38 (3H) s; 2.31 (6H) s; 2.20 (6H) s; 1.26 (3H) s.

The reductive alkylation procedure of Example 14 can also be employed to prepare the following compounds by substitution of the appropriately esterified 8,8a-deoxy-8-azidomethyloleandomycin for the oleandomycin compound 9 of Example 14 and by substituting the appropriate amount of n-alkanol for formaldehyde:

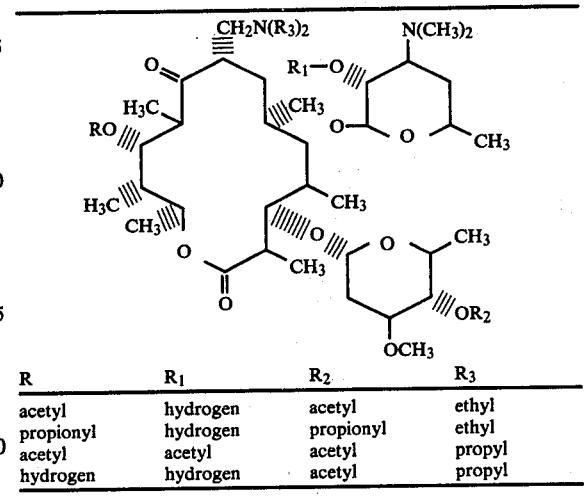

| R | R$_1$ | R$_2$ | R$_3$ |
|---|---|---|---|
| acetyl | hydrogen | acetyl | ethyl |
| propionyl | hydrogen | propionyl | ethyl |
| acetyl | acetyl | acetyl | propyl |
| hydrogen | hydrogen | acetyl | propyl |

In these cases, use of a solution of the appropriate amount of aldehyde in methanol, instead of water as was done in Example 14, will be the method of choice.

EXAMPLE 15

8,8a-Deoxy-8-(N-benzoyl)-aminomethyl-4″-acetyloleandomycin 15

To a solution of 500 mg. (0.685 mmoles) of 8,8a-deoxy-8-aminomethyl-4″-acetyloleandomycin 11 in 100 ml. of 25% by volume aqueous tetrahydrofuran was added one normal aqueous sodium hydroxide to adjust the pH to 9. To this basic solution was then dropwise added a solution of 240 mg. (1.71 mmoles) benzoyl chloride in 30 ml. dry THF and the solution stirred until reaction was essentially complete according to the difference in Rf of the product and starting material spots on thin layer chromatography. The THF was then removed in vacuo and the resultant aqueous layer was covered with 100 ml. ethyl acetate while maintaining the aqueous layer at pH 9. After extracting the aqueous layer with 2×50 ml. portions of the ethyl acetate, the organic layers were combined, dried over magnesium sulfate and filtered to remove the drying agent. Removal of the solvent from the filtrate by vacuum evaporation yielded a residue which was chromatographed on a 25 g. column of silica gel packed in chloroform. Elution with chloroform and then with 2% methanol in chloroform followed by removal of the solvent from the product fractions allowed the isolation of 270 mg. of the title compound. It exhibited the following characteristic reasonances in the NMR:

NMR (CDCl$_3$) δppm: 7.50 (5H) m; 6.90 (1H) m; 5.28 (1H) m; 3.36 (3H) s; 2.30 (6H) s; 2.16 (3H) s.

EXAMPLE 16-18

8,8a-Deoxy-8-(N-acyl or sulfonyl)aminomethyl-4″-acetyloleandomycin

The following compounds were prepared according to the procedure of Example 15 by substitution of the appropriate carboxylic acid or sulfonyl chloride in place of benzoyl chloride.

| Ex. No. | Acyl A or sulfonyl B | NMR (partial spectrum) δppm CDCl$_3$ |
|---|---|---|
| 16 | A = α-thienoyl compound 16 | δ7.46(3H)m; δ6.73(1H)m; δ5.26(1H)m; δ3.36(3H)s; δ2.30(6H)s; δ2.20(3H)s. |
| 17 | A = nicotinyl compound 17 | δ8.10(1H)m; δ7.26(3H)m; δ5.08(1H)m; δ3.36(3H)s; δ2.30(6H)s; δ2.10(3H)s. |
| 18 | B = methyl sulfonyl compound 18 | δ7.03(1H)bs; δ5.45(1H)m; δ3.40(3H)s; δ3.00(3H)s; δ2.30(6H)s; δ2.13(3H)s. |

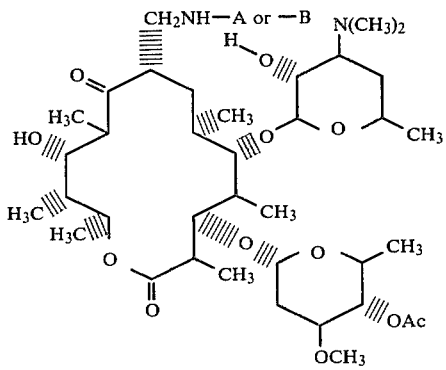

oleandomycin compounds 16, 17 and 18

The following oleandomycins can also be prepared according to the procedure of Example 15 by substitution of the appropriately esterified 8,8a-deoxy-8-aminomethyloleandomycin for the starting oleandomycin compound 11 of Example 15 and by substitution of the appropriate carboxylic acid chloride for benzoyl chloride.

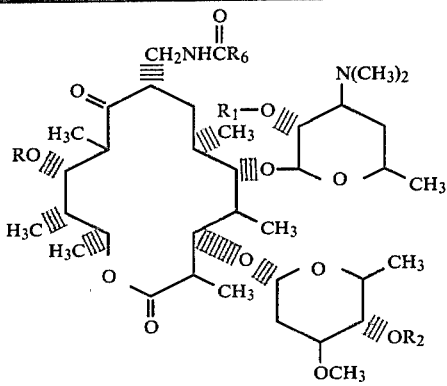

| R | R$_1$ | R$_2$ | R$_6$ |
|---|---|---|---|
| acetyl | acetyl | acetyl | phenyl |
| propionyl | hydrogen | propionyl | p-chlorophenyl |
| acetyl | hydrogen | propionyl | propyl |
| acetyl | hydrogen | acetyl | p-trifluoromethylphenyl |
| hydrogen | hydrogen | acetyl | p-methoxyphenyl |
| hydrogen | hydrogen | propionyl | m-trifluoromethylphenyl |
| hydrogen | acetyl | acetyl | o-nitrophenyl |
| hydrogen | propionyl | propionyl | m-ethylphenyl |
| propionyl | hydrogen | propionyl | propyl |
| acetyl | hydrogen | acetyl | pentyl |
| acetyl | acetyl | acetyl | p-carboxyethylphenyl |
| acetyl | hydrogen | acetyl | m-hydroxyphenyl |
| propionyl | hydrogen | propionyl | o-carbamoylphenyl |
| hydrogen | acetyl | acetyl | picolinyl |
| propionyl | propionyl | propionyl | isonicotinyl |

The following oleandomycins can also be prepared according to the procedure of Example 15 by substitution of the appropriately esterified 8,8a-deoxy-8-aminomethyloleandomycin for the starting oleandomycin compound 11 of Example 15 and by substitution of the appropriate sulfonyl chloride for benzoyl chloride.

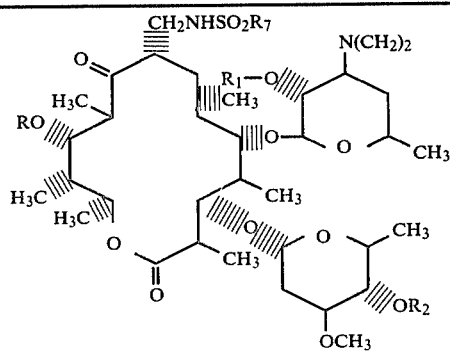

| R | R$_1$ | R$_2$ | R$_7$ |
|---|---|---|---|
| acetyl | acetyl | acetyl | phenyl |
| acetyl | acetyl | acetyl | propyl |
| hydrogen | hydrogen | propionyl | m-ethylphenyl |
| hydrogen | propionyl | propionyl | p-trifluoromethylphenyl |
| acetyl | hydrogen | acetyl | methyl |
| hydrogen | hydrogen | acetyl | m-trifluoromethylphenyl |

EXAMPLE 19

8,8a-Deoxy-8-(N-acetyl)aminomethyl-4″-acetyloleandomycin 19

To a solution of 500 mg. (0.685 mmoles) 8,8a-deoxy-8-aminomethyl-4″-acetyloleandomycin 11 in 5 ml. methanol was dropwise added 75 mg. (0.75 mmoles)

acetic anhydride in 0.5 ml. methanol. After being allowed to stir for 30 minutes, a thin layer chromatograph of a sample of the starting oleandomycin and the reaction solution was developed and showed no remaining starting oleandomycin. To the reaction solution was then added 20 ml. water and 50 ml. ethyl acetate while adjusting the pH of the aqueous phase to nine. The aqueous phase was extracted with 2×30 ml. ethyl acetate and the combined organic layers were dried over magnesium sulfate. Removal of the drying agent by suction filtration followed by removal of the solvent from the filtrate in vacuo gave a residue which was chromatographed on a 40×3.5 cm. column of silica gel. Elution with chloroform and 2% methanol in chloroform allowed separation and purification of 340 mg. of the title compound. It had the following chacteristic resonances in the NMR spectrum:

NMR (CDCl₃) δppm: 6.15 (1H) m; 5.33 (1H) m; 3.36 (1H) s; 2.28 (6H) s; 2.10 (3H) s; 1.90 (3H) s.

The following oleandomycins can also be prepared according to the procedure of Example 19 by substitution of the appropriately esterified 8,8a-deoxy-8-aminomethyloleandomycin for the starting oleandomycin compound 11 of Example 19 and of the appropriate anhydride for acetic anhydride.

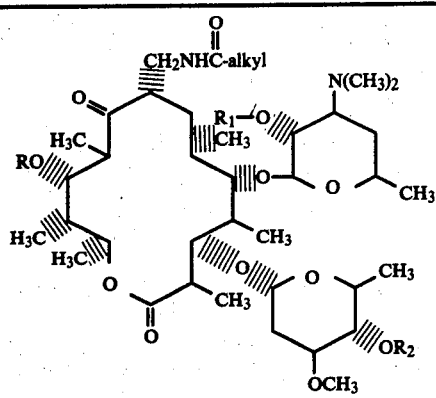

| R | R₁ | R₂ | alkyl |
|---|---|---|---|
| acetyl | acetyl | acetyl | propyl |
| acetyl | hydrogen | hydrogen | ethyl |
| propionyl | propionyl | propionyl | butyl |

EXAMPLE 20

8,8a-Deoxy-8-(N-formyl)aminomethyl-4"-acetyloleandomycin 20

By use of the procedure of Example 19, oleandomycin 11 was formylated by substitution of the appropriate amount of acetic formic anhydride for acetic anhydride to produce the title compound. It had the following characteristic resonances in the NMR spectrum:

NMR (DCCl₃) δppm: 8.08 (1H) m; 6.96 (1H) s; 5.30 (1H) m; 3.38 (3H) s; 2.30 (6H) s; 2.11 (3H) s.

By employing the procedure of Example 20, the following compounds can be prepared by substituting the appropriately esterified 8,8a-deoxy-8-aminomethyloleandomycin for the starting oleandomycin compound 11 of Example 20: 8,8a-deoxy-8-(N-formyl)aminomethyl-4"-propionyloleandomycin, 8,8a-deoxy-8-(N-formyl)aminomethyl-4",11-diacetyloleandomycin, 8,8a-deoxy-8-(N-formyl)aminomethyl-2',4"-dipropionyloleandomycin and 8,8a-deoxy-8-(N-formyl)aminomethyl-4",11-dipropionyloleandomycin.

EXAMPLE 21

8,8a-Deoxy-8-N-(dimethylaminomethylidenyl)aminomethyl-4"-acetyloleandomycin

To a solution of 500 mg. (0.685 mmoles) 8,8a-deoxy-8-aminomethyl-4"-acetyloleandomycin 11 in 20 ml. dry DMF at 0° C. and under a nitrogen atmosphere was added 244.5 mg. (2.05 mmoles) dimethylformamidedimethylacetal by syringe and septum cap at such a rate so as to maintain the temperature at 0° C. After the addition was complete, the solution was allowed to stir at 0° C. for 5 minutes and then warmed to ambient temperature. After stirring under a nitrogen atmosphere for one hour, a thin layer chromatographic comparison of the starting oleandomycin and the reaction solution revealed that no starting compound was left. The reaction solution was then poured onto ice (50 g.) and extracted with 100 ml. of ethyl acetate. The organic layer was extracted twice with 50 ml. water and once with 50 ml. saturated brine, dried over sodium sulfate, filtered to remove the drying agent and the solvent removed in vacuo from the filtrate to yield 500 mg. of the title compound. It had the following characteristic resonances in the NMR spectrum:

NMR (DCCl₃) δppm: 7.00 (1H) s; 5.48 (1H) m; 3.36 (3H) s; 2.80 (6H) s; 2.10 (3H) s.

The following compounds can be prepared according to the procedure of Example 21 by use of the appropriately esterified 8,8a-deoxy-8-aminomethyloleandomycin and the appropriate dialkyl formamide dimethyl acetal: 8,8a-deoxy-8-(diethylaminomethylidenyl)aminomethyl-4",11-dipropionyloleandomycin and 8,8a-deoxy-8-(dipropylaminomethylidenyl)aminomethyl-4"-acetyloleandomycin.

EXAMPLE 22

8,8a-Deoxy-8-ureidomethyl-4"-acetyloleandomycin 22

To a solution of 500 mg. (0.685 mmoles) 8,8a-deoxy-8-aminomethyl-4"-acetyloleandomycin 11 in 50 ml. benzene was added a solution of isocyanic acid in 10 ml. benzene which had been previously prepared by addition of 391 mg. (3.42 mmoles) of trifluoroacetic acid to 246.5 mg. (3.42 mmoles) sodium isocyanate in 10 ml. benzene and subsequent exclusion of the resultant precipitate. After stirring for one hour, the entire solution was poured into a two-phase mixture of 100 ml. ethyl acetate and 50 ml. water while adjusting the pH to nine. The aqueous phase was extracted with 2×30 ml. ethyl acetate and the combined organic layers were dried over sodium sulfate. Removal of the drying agent by suction filtration followed by removal of the solvent from the filtrate in vacuo gave a residue which was chromatographed on a 150 g. silica gel column. Elution with chloroform allowed purification producing 580 mg. of the title compound. It had the following characteristic resonance in the NMR spectrum:

NMR (DCCl₃) δppm: 5.48 (1H) m; 3.41 (3H) s; 2.36 (6H) s; 2.16 (3H) s.

EXAMPLE 23

8,8a-Deoxy-8-(N-phenylureido)methyl-4"-acetyloleandomycin 23

By employing the procedure of Example 22, oleandomycin 11 was converted into the title compound 23 by substitution of phenylisocyanate for isocyanic acid.

The title compound had the following characteristic resonances in the NMR spectrum.

NMR (DCCl$_3$) $\delta$ppm: 7.20 (5H) m; 5.40 (1H) m; 3.36 (3H) s; 2.30 (6H) s; 2.13 (3H) s.

Following the procedure of Example 23, the following compounds can be prepared by employment of the appropriately esterified 8,8a-deoxy-8-aminomethyloleandomycin for the starting oleandomycin 11 of Example 11 and by the use of the appropriate alkylisocyanate instead of phenylisocyanate.

| R | R$_1$ | R$_2$ | alkyl |
|---|---|---|---|
| acetyl | acetyl | acetyl | methyl |
| propionyl | hydrogen | propionyl | propyl |
| hydrogen | hydrogen | acetyl | butyl |

EXAMPLE 24

8,8a-deoxy-8-(imidazol-1-yl)methyl-4"-acetyloleandomycin

To a solution of 2.5 g. (2.8 mmoles) 8,8a-deoxy-8-tosyloxymethyl-4"-acetyl oleandomycin 8 in 25 ml. dimethylsulfoxide was added 1.906 g. (28 mmoles) imidazole as a solid. The solution was warmed to 50° C. and allowed to stir for 65 hours. After cooling, the reaction solution was then poured into a two phase mixture of 50 ml. water and 100 ml. ethyl acetate while adjustment of the pH to 9.5 was made. The organic layer was washed with two portions of 25 ml. each water and one of 25 ml. saturated brine. The organic layer was dried over magnesium sulfate, filtered to remove the drying agent and the solvent removed in vacuo from the filtrate. The resulting residue was chromatographed on a 50 g. column of silica gel packed in chloroform. Elution with chloroform and 5% methanol in chloroform allowed separation and purification of 1.0 g. of the title compound. It had the following characteristic resonance in the NMR spectrum:

NMR (CDCl$_3$) $\delta$ppm: 7.55 (1H) s; 7.00 (2H) bs; 5.46 (1H) m; 3.40 (3H) s; 2.33 (6H) s; 2.13 (3H) s.

The following compounds can be prepared using the procedure of Example 24 by substituting the appropriately esterified 8,8a-deoxy-8-tosyloxymethyloleandomycin for the starting oleandomycin compound 8 of Example 24:

8,8a-deoxy-8-(imidazol-1-yl)methyl-4"-propionyloleandomycin and 8,8a-deoxy-8-(imidazol-1-yl)methyl-4",11-diacetyloleandomycin.

What is claimed is:

1. A compound of the structure:

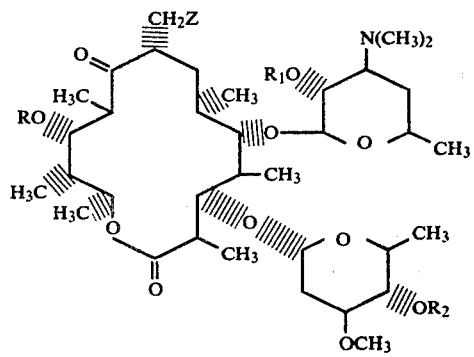

and the pharmaceutically acceptable acid addition salts thereof wherein:

R is selected from the group consisting of hydrogen and n-alkanoyl having from two to three carbon atoms;

R$_1$ is selected from the group consisting of hydrogen and n-alkanoyl having from two to three carbon atoms;

R$_2$ is selected from the group consisting of hydrogen and n-alkanoyl having from two to three carbon atoms; and Z is —Cl.

2. The compound according to claim 1 wherein R and R$_1$ are each hydrogen and R$_2$ is acetyl.

* * * * *